United States Patent
Zhu et al.

(10) Patent No.: US 10,368,541 B2
(45) Date of Patent: Aug. 6, 2019

(54) URINE PRESERVATIVE REAGENT FOR MICROFILTRATION

(71) Applicant: Creatv MicroTech, Inc., Potomac, MD (US)

(72) Inventors: Peixuan Zhu, Derwood, MD (US); Daniel Adams, Basking Ridge, NJ (US); Cha-Mei Tang, Potomac, MD (US)

(73) Assignee: CREATV MICROTECH, INC., Potomac, MD (US)

( * ) Notice: Subject to any disclaimer, the term of this patent is extended or adjusted under 35 U.S.C. 154(b) by 323 days.

(21) Appl. No.: 14/776,194

(22) PCT Filed: Mar. 13, 2014

(86) PCT No.: PCT/US2014/025728
§ 371 (c)(1),
(2) Date: Sep. 14, 2015

(87) PCT Pub. No.: WO2014/151437
PCT Pub. Date: Sep. 25, 2014

(65) Prior Publication Data
US 2016/0021872 A1  Jan. 28, 2016

Related U.S. Application Data

(60) Provisional application No. 61/787,118, filed on Mar. 15, 2013.

(51) Int. Cl.
*A01N 1/02* (2006.01)
*G01N 33/493* (2006.01)
*G01N 33/574* (2006.01)

(52) U.S. Cl.
CPC ........... *A01N 1/021* (2013.01); *A01N 1/0215* (2013.01); *G01N 33/493* (2013.01); *G01N 33/574* (2013.01)

(58) Field of Classification Search
CPC .... A01N 1/021; A01N 1/0215; G01N 33/493; G01N 33/574
See application file for complete search history.

(56) References Cited

U.S. PATENT DOCUMENTS

| | | | |
|---|---|---|---|
| 5,679,333 A | 10/1997 | Dunphy | |
| 5,849,517 A * | 12/1998 | Ryan | G01N 1/30 435/40.5 |
| 8,178,296 B2 | 5/2012 | Lader | |
| 2010/0222333 A1* | 9/2010 | Maitre | A61K 9/0014 514/222.2 |
| 2013/0059330 A1 | 3/2013 | Peltier | |

FOREIGN PATENT DOCUMENTS

| | | | |
|---|---|---|---|
| WO | 98-02740 | | 1/1998 |
| WO | 2011-103114 | | 8/2011 |
| WO | WO 2011/092414 | * | 8/2011 |

OTHER PUBLICATIONS

Kiernan, "Formaldehyde, formalin, paraformaldehyde and glutaraldehyde: What they are and what they do," Microscopy Today Jan. 2000, pp. 8-12 (2000).*

A printout retrieved from http://msdssearch.dow.com/PublishedLiteratureDOWCOM/dh_0889/0901b80380889773.pdf?filepath=polyglycols/pdfs/noreg/118-01802.pdf&from Page=GetDoc on Sep. 25, 2017.*

International Search Report dated Jul. 4, 2014 in corresponding International Application No. PCT/US2014/025728.

* cited by examiner

*Primary Examiner* — Galina M. Yakovleva
(74) *Attorney, Agent, or Firm* — Wenderoth, Lind & Ponack, L.L.P.

(57) ABSTRACT

A preservative reagent for urine is disclosed that increases the stability of cells, such as tumor cells, in urine for a period of several weeks. The preservative reagent comprises polyethylene glycol (PEG), ethanol, paraformaldehyde (PFA), and ethylenediaminetetraacetic acid (EDTA), and optionally pH stabilizing reagents.

8 Claims, No Drawings

URINE PRESERVATIVE REAGENT FOR MICROFILTRATION

TECHNICAL FIELD

This invention relates to a preservative reagent useful for stabilizing and preserving cells, such as normal cells and tumor cells, in urine specimens. This invention also relates to methods of preserving urine samples using the preservative reagent, and to collection of cells from the preserved urine.

BACKGROUND

Urine sample preparation is key factor in obtaining adequate and representative cells for downstream analysis. Current methodology is usually a centrifugation for separation of tumor cells from urine based on their densities. However, this method often collects all types of cells and particles, and the recovery of the cells for subsequent molecular analysis is limited. Recent advances in size-selective microfiltration technology provide an alternative approach for isolation of tumor cells from urine sample. CellSieve™ is a new microfilter membrane that has been developed by Creatv MicroTech, Inc. The CellSieve™ membrane contains a high density of pores with selective sizes, which can separate tumor cells from both blood cells and contaminated particles based on size differences. During the microfiltration process, blood cells and contaminants, which are smaller than the size of the pores, can pass through the filter membrane, whereas tumor cells, which are usually larger than the size of the pores, will be captured on the filter. The microfiltration system can produce a high recovery efficiency of tumor cells as well as a reduction in any cross-contaminations to low levels.

Analysis of tumor cells is often necessary in the diagnosis and treatment of urological cancers. In such analyses, cell morphology, protein expression and molecular alternations of the tumor cells are frequently sought to be determined. However, if urine is permitted to be collected in a clinical site and then transported to a central lab, the urine sample will often be stored at either room temperature or 4° C. for a prolonged period of hours before microfiltration and subsequent analysis can be completed. As a result, the morphology of the tumor cells in urine will frequently change due to cell lysis or apoptosis. In addition, the chemical composition of the urine sample is frequently altered upon standing as a result of environmental changes, for example, temperature change and protease digestion. Furthermore, bacterial contamination and other microorganisms may grow in urine, which may alter microfiltration and downstream analysis.

Many of the previously described preservative reagents are not compatible with the microfiltration system because they may contain organic solvents or high concentrations of acids, which may damage the microfilter membrane. For examples, methanol and glacial acetic acid can preserve some analytes in urine but they can also dissolve or damage the microfilter membrane. In addition, inclusion of methanol and high concentrations of acid comes with safety concerns to the users due to the characteristics of the hazard materials. As the results, there is a need for an effective preservative reagent that can stabilize tumor cells in urine specimen for the microfiltration.

SUMMARY

The present invention is directed to a preservative reagent for stabilizing and preserving cells, such as normal cells and tumor cells, in urine specimens and methods of using the reagent. Upon combining a urine sample and the preservative reagent, the resulting solution can be analyzed either immediately or at a later time. Techniques such as microfiltration can be used for isolation and identification of tumor cells in the solution. More particularly, the invention provides a preservative which may be added to urine specimens containing normal cells and tumor cells from urinary tract cancers, such as bladder cancer, kidney cancer, prostate cancer, ureter cancer and urethra cancer, for subsequent microfiltration, immunochemical and molecular analyses.

The present invention is directed, in part, to a novel preservative reagent. Upon addition to a urine sample, cells in the sample, such as tumor cells, remain in an unaltered state for a period of time sufficient to allow analysis of the sample and cells therein when convenient for the researcher or laboratory performing the analysis.

The preservative reagent comprises (i) polyethylene glycol (PEG), (ii) ethanol, (iii) paraformaldehyde (PFA), and (iv) ethylenediaminetetraacetic acid (EDTA). The reagent is stabilized using pH stabilizing reagents. The preservative reagent can be prepared by mixing the four major components and then adjusting the pH using the pH stabilizing reagents.

In a first embodiment, the present invention is directed to a preservative reagent comprising (i) PEG, (ii) ethanol, (iii) PFA, and (iv) EDTA.

In a second embodiment, the invention is directed to a preservative reagent comprising (i) PEG, (ii) ethanol, (iii) PFA, (iv) EDTA, and (v) one or more pH stabilizing reagents.

In a third embodiment, the invention is directed to a preservative reagent comprising 0.2-20% PEG, 25-75% ethanol, 0.04-4% PFA, and 2-200 mM EDTA. In some aspects of this embodiment, the pH of the reagent is adjusted using pH stabilizing reagents. In these aspects, the pH is adjusted to a range of pH 4.0-10.0, more preferably in a range of 7.3-7.5, and preferably at pH 7.4.

In a fourth embodiment, the invention is directed to a preservative reagent comprising 0.5-5% PEG, 40-60% ethanol, 0.01-2% PFA, and 5-50 mM EDTA. In some aspects of this embodiment, the pH of the reagent is adjusted using pH stabilizing reagents. In these aspects, the pH is adjusted to a range of pH 4.0-10.0, more preferably in a range of 7.3-7.5, and preferably at pH 7.4.

In a fifth embodiment, the invention is directed to a preservative reagent comprising 2% PEG-1450, 50% ethanol, 0.4% PFA, and 20 mM EDTA. In some aspects of this embodiment, the pH of the reagent is adjusted using pH stabilizing reagents. In these aspects, the pH is adjusted to a range of pH 4.0-10.0, more preferably in a range of 7.3-7.5, and preferably at pH 7.4.

In a sixth embodiment, the invention is directed to methods for preparing a preserved urine sample comprising adding a preservative reagent of the present invention to urine, wherein the ratio of the preservative reagent to urine in the sample is from about 0.1:20 to about 10:0.2 (vol:vol). In particular aspects of this embodiment, the ratio of the preservative reagent to urine in the sample is from about 0.5:4 to about 2:1 (vol:vol). In a specific aspect, the ratio of the preservative reagent to urine in the sample is about 1:2 (vol:vol).

In a seventh embodiment, the invention is directed to collecting cells from the preserved urine samples. This can be accomplished by a variety of methods including, but not limited to filtration, antibody capture, collection of pellet after spin down, etc. Also, collection of the cells in sample by a combination of the methods.

DETAILED DESCRIPTION

The present invention is directed to a preservative reagent and methods for using the same in preparing a preserved urine sample. The preservative reagent comprises (i) PEG, (ii) ethanol, (iii) PFA, and (iv) EDTA. The preservative reagent may be stabilized using pH stabilizing reagents.

Features and benefits of the invention:
1. The preservative reagent of the invention is available as a liquid format in urine collection and preservative tubes.
2. The preservative reagent eliminates the need to immediately process microfiltration of urine samples, and allows urine samples to be stored at 4° C. for several weeks or shipped to centralized testing facilities at ambient temperatures.
3. The preservative reagent prevents the growth of bacteria and fungi, and also inactivates viral pathogens in urine, allowing the preservative-treated samples to be handled and shipped safely.
4. The preservative reagent increases the stability of cells, such as tumor cells, in urine. The cells can be separated from preserved urine samples using a number of different methods, including CellSieve™ microfiltration method.

Preservative Reagent

The skilled artisan will appreciate that the source and identity of the particular components included in the reagent may vary depending on the characteristics of the component. For example, the PEG used in the reagent may vary in molecular weight. An acceptable PEG for use in the reagents of the invention includes PEG-1450 (e.g., Sigma-Aldrich, St. Louis, Mo.; Catalog Number P5402-500G). Other acceptable PEG materials for use in the preservative reagents of the invention are PEGs in a range of molecular weights from 200 to 511,000, including, but not limited to, PEG-200, PEG-300, PEG-400, PEG-600, and PEG-1,000, PEG-1,500, PEG-2,000. PEG-3,000, PEG-6,000, and PEG-8,000. Ethanol is commercially available as an absolute solution (e.g., Fish Scientific, Pittsburgh, Pa.; Catalog Number BP2818-500). EDTA is commercially available as a dry chemical type (e.g., Sigma-Aldrich, St. Louis, Mo.; Catalog Number E6758-500G) or as a 0.5 M pre-dissolved solution (e.g., Fish Scientific, Pittsburgh, Pa.; Catalog Number 50-230-4730). PFA also is commercially available as a dry chemical type (e.g., Sigma-Aldrich, St. Louis, Mo.; Catalog Number P6148-500G).

The skilled artisan will further appreciate that the specific amounts of the four components can vary without departing from the excellent properties of the resulting preservative reagent. The amount of PEG in the reagent may vary from between about 0.2 and about 20% (wt/vol), and includes 0.5-15% (wt/vol), 1-10% (wt/vol), 1.5-7.5% (wt/vol), 0.2-10% (wt/vol), 0.2-5% (wt/vol), 0.2-4% (wt/vol), 0.5-20% (wt/vol), 1-20% (wt/vol) and 1.5-20% (wt/vol). Specific amounts of PEG include about 0.5%, 1%, 1.5%, 2%, 2.5%, 3%, 3.5%, and 4%.

The amount of ethanol in the reagent may vary from between about 25 and about 75% (vol/vol), and includes 30-70% (vol/vol), 35-65% (vol/vol), 40-60% (vol/vol), 45-55% (vol/vol), 25-65% (vol/vol), 25-60% (vol/vol), 25-55% (vol/vol), 30-70% (vol/vol), 35-70% (vol/vol), 40-70% (vol/vol), and 45-70% (vol/vol). Specific amounts of ethanol include about 40%, 45%, 50%, 55%, and 60%.

The amount of PFA in the reagent may vary from between about 0.04 and about 4% (wt/vol), and includes 0.1-3% (wt/vol), 0.2-2% (wt/vol), 0.3-1% (wt/vol), 0.04-3% (wt/vol), 0.04-2% (wt/vol), 0.04-1% (wt/vol), 0.04-0.5% (wt/vol), 0.1-4% (wt/vol), 0.2-4% (wt/vol), 0.3-4% (wt/vol), and 0.35-4% (wt/vol). Specific amounts of PFA include about 0.1%, 0.2%, 0.3%, 0.4%, 0.5%, 0.6%, 0.7%, and 0.8%.

The amount of EDTA in the reagent may vary from between about 2 and about 200 mM, and includes 5-100 mM, 10-50 mM, 15-40 mM, 2-150 mM, 2-100 mM, 2-50 mM, 2-40 mM, 2-30 mM, 5-200 mM, 10-200 mM, and 15-200 mM. Specific amounts of PFA include about 10 mM, 15 mM, 20 mM, 25 mM, and 30 mM.

In a specific aspect, the preservative reagent comprises 1-3% PEG, 45-55% ethanol, 0.1-1% PFA, and 10-30 mM EDTA. In another specific aspect, the preservative reagent comprises 2% PEG-1450, 50% ethanol, 0.4% PFA, and 20 mM EDTA.

The preservative reagent may be prepared by individually dissolving each of PEG, PFA and EDTA in deionized water, and then mixing selected amounts of the solutions with ethanol. The pH of the reagent may be stabilized by adjusting it to between about 4.0 and about 10.0, including, 4.0, 4.5, 5.0, 5.5, 6.0, 6.5, 7.0, 7.1, 7.2, 7.3, 7.4, 7.5, 7.6, 7.7, 7.8, 7.9, 8.0, 8.5, 9.0, 9.5 and 10.0. In specific aspect, the pH is adjusted to about 7.4. The pH stabilizing reagents will be known to the skilled artisan, but suitable pH stabilizing reagents for use in the reagents of the present invention include phosphate buffered saline (PBS), Tris-HCl, Hepes, citrate, and carbonate buffers, etc Preservation of Cells in Urine Upon mixing a preservative reagent of the present invention with urine, the preservative reagent acts as a urine preservative that maintains original morphology of cells, such as tumor cells, and inhibits decomposition of DNA, RNA and microRNA in the cells. Typically, the preservative reagent is mixed with urine within about 10, 9, 8, 7, 6, 5, 4, 3, 2 or 1 hour of collecting the sample of urine from a subject, or within about 60, 55, 50, 45, 40, 35, 30, 25, 20, 15, 10, 9, 8, 7, 6, 5, 4, 3, 2 or 1 minutes of collecting the sample of urine from the subject. In particular aspects, the reagent is mixed with the sample within about 3 hours, and preferably within 20 minutes, of collecting the urine sample from the subject. When the preservative reagent is not mixed with urine immediately following collection from a subject, the urine typically will be chilled on ice or stored at 4° C. to inhibit cell lysis prior to mixing the urine with the reagent.

The skilled artisan will also appreciate that the ratio of the preservative reagent to urine can vary. However, the ratio of reagent to urine will be from about 0.1:20 to about 10:0.2 (vol:vol), and includes a ratio of reagent to urine of from about 0.5:4 to about 2:1 (vol:vol), and particular ratios that include, but are not limited to 0.5:2.5, 0.75:2.25, 1:2, 1.25:1.75, and 1.5:1.5 (vol:vol). In a particular aspect, the ratio of reagent to urine is 1:2 (vol:vol).

Upon mixing the preservative reagent with the urine, the preserved urine may be stored at 4° C. until analyzed. Alternatively, the preservative urine may be stored at room temperature, frozen, or stored at a temperature between 0° C. and room temperature, such as at 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., or higher.

Collection of Cells from Urine Sample

Many methods can be used for isolation of cells from the preserved urine. Centrifugation is one of the most common methods and involves use of centrifugal force for sedimentation of heterogeneous mixtures in the preserved urine. However, the pelleted materials at the bottom of centrifuge tube could contain not only cells, but also contaminating protein precipitates, cellular materials, red blood cells, and bacteria, etc.

Another method is to use antibodies or aptamers against the markers on the surface of cells to improve the purity of the collected material. Antibodies and aptamers can be attached to a solid support such as magnetic beads, ferrofluids, surfaces of microfluidic channels, etc. Magnetic beads or ferrofluids, coated with antibodies that recognize the cell surface marker of interest, can be mixed with preserved urine or a pellet collected from preserved urine. The cells will be captured on the surfaces of the magnetic beads or ferrofluids during incubation. Magnets can be used to collect the magnetic beads and ferrofluids and collect the cells of interest. If the antibodies or aptamers are coated on the surface of a microfluidic chip, the cells of interest will be captured on the surface of the microfluidic chip when the preserved urine flows through the chip. An example of epithelial surface marker suitable for use in the collection of cells from preserved urine is epithelial cell adhesion molecule (EpCAM). Bladder cells and bladder cancer cells express EpCAM on the surface of the cells.

Another method of affinity capture is to incubate the preserved urine or pellet from preserved urine with antibody (antibodies) and/or aptamers, specific for cell surface markers of interest, that are conjugated with either avidin or biotin. After incubation, the cells can be collected on surfaces coated with biotin or avidin, respectively, to form biotin/avidin pairs. The surfaces can be magnetic beads, ferrofluids, microfluidic chips, etc.

A rapid and simple method to collect cells from the preserved urine is to use a filter with pore size smaller than the cells of interest. Epithelial cells are typically larger than 7 microns. Proteins, cellular debris, red blood cells and bacteria will pass through pores as small as 3-4 microns in diameter. Thus, filtration is a method to collect cells of interest with low contamination.

There are a wide variety of filters available for use in cellular collection. The properties of the filters most suitable for collecting cells are clear, non-fluorescent, and strong. Another desirable property is uniform size and distribution without overlapping pores. The filter that satisfies all those properties is made by a lithographical method using photodefinable dry films. A commercial product having the brand name CellSieve™ (Creatv MicroTech, Inc., Potomac, Md.) is an example of a suitable filter for use in the collection of cells from preserved urine samples.

Examples

The preservative reagent was found to increase the stability of tumor cells in urine. For this example, the preservative reagent comprised 2% PEG-1450, 0.4% PFA, 20 mM EDTA, and 50% ethanol. Two bladder cancer cell lines, T24 and RT4 were used for spiking experiments. The cell line was cultured in modified McCoy's medium supplemented with 10% bovine fetal serum according to ATCC's protocol. Cell suspension was prepared by standard trypsin-treatment method. Total cell counts were determined manually with a hemocytometer. A middle stream of urine sample from a healthy donor was collected for the spiking experiments. This urine sample was centrifuged at 600×g for 10 min to remove contaminated cells and particles. The urine supernatant was aliquot in 50 mL BD Falcon tubes, 33 mL of urine per tube.

Bladder cancer T24 and RT4 cells were spiked in the urine aliquot, respectively. The spiked sample (33 mL) was mixed with 17 mL of the noted preservative reagent to a total volume of 50 mL. A non-treated control was included by mixing 33 mL of the spiked urine with 17 mL sterile PBS buffer. By using a hemocytometer, cell concentration of T24 was determined approximately $1.5 \times 10^5$ cells/mL and the concentration of RT4 was approximately $9.9 \times 10^4$ cells/mL. These were initial concentrations of input cells at Day 0. The preservative reagent-treated and non-treated (PBS control) samples were stored at 4° C. for four weeks.

After the storage, the bladder cancer cells were fast degraded in the PBS controls. On Day 28, there were only 0.1% and 0.05% of input T24 and RT4 cells were retained, respectively. In contrast, bladder cancer cells were stable in urine samples treated with the noted preservative reagent. 99.04% and 99.49% of input T24 and RT4 cells, respectfully, could be retained for four weeks. The cells were collected by filtration using CellSieve™ microfilters produced by lithographic method. In addition, the bladder cancer cells maintained their original morphology. This demonstrated that the noted preservative reagent could efficiently increase the stability of bladder cancer cells in urine. By using the noted preservative reagent, urine sample can be stored over a long-term period or transported from clinical setting to central lab for further microfiltration and downstream analysis.

What is claimed is:

1. A preservative reagent comprising a mixture of 2% (wt/vol) polyethylene glycol 1450 (PEG-1450), 50% (vol/vol) ethanol, 0.4% (wt/vol) paraformaldehyde (PFA), and 20 mM ethylenediaminetetraacetic acid (EDTA).

2. The preservative reagent of claim 1, further comprising one or more pH stabilizing reagents.

3. The preservative reagent of claim 2, wherein the pH of the preservative reagent is in a range of pH 4.0-10.0.

4. A method for preparing a preserved urine sample comprising adding a preservative reagent of claim 1 to urine, wherein the ratio of the preservative reagent to urine in the sample is from about 0.1:20 to about 10:0.2 (vol:vol).

5. The method of claim 4, wherein the ratio of the preservative reagent to urine in the sample is from about 0.5:4 to about 2:1 (vol:vol).

6. The method of claim 4, wherein the ratio of the preservative reagent to urine in the sample is about 1:2 (vol:vol).

7. A method of collecting cells from a preserved urine sample, comprising
   (a) preparing a preserved urine sample by adding a preservative reagent of claim 1 to urine, wherein the ratio of the preservative reagent to urine in the sample is from about 0.1:20 to about 10:0.2 (vol:vol), and
   (b) collecting cells from the preserved urine sample of (a).

8. The method of claim 7, wherein the cells are collected using one or more of an antibody attached to a solid support, an aptamer attached to a solid support, and a filter.

* * * * *